(12) United States Patent
Melnykowycz et al.

(10) Patent No.: US 10,548,488 B2
(45) Date of Patent: Feb. 4, 2020

(54) METHOD FOR PRODUCING A STRAIN GAUGE DEVICE

(71) Applicants: STBL MEDICAL RESEARCH AG, Wollerau (CH); EMPA SWISS FEDERAL LABORATORIES FOR MATERIALS SCIENCE AND TECHNOLOGY, Duebendorf (CH)

(72) Inventors: Mark Melnykowycz, Winterthur (CH); Frank Clemens, Frauenfeld (CH)

(73) Assignees: STBL Medical Research AG, Wollerau (CH); EMPA Swiss Federal Laboratories for Materials Science and Technology, Duebendorf (CH)

( * ) Notice: Subject to any disclaimer, the term of this patent is extended or adjusted under 35 U.S.C. 154(b) by 115 days.

(21) Appl. No.: 15/555,934

(22) PCT Filed: Feb. 16, 2016

(86) PCT No.: PCT/EP2016/053239
§ 371 (c)(1),
(2) Date: Sep. 5, 2017

(87) PCT Pub. No.: WO2016/142130
PCT Pub. Date: Sep. 15, 2016

(65) Prior Publication Data
US 2018/0049655 A1    Feb. 22, 2018

(30) Foreign Application Priority Data
Mar. 12, 2015 (EP) .................................... 15158800

(51) Int. Cl.
*H01C 17/28* (2006.01)
*A61B 5/021* (2006.01)
(Continued)

(52) U.S. Cl.
CPC .......... *A61B 5/02141* (2013.01); *A61B 5/681* (2013.01); *G01L 1/22* (2013.01);
(Continued)

(58) Field of Classification Search
CPC .......... A61N 1/36014; A61H 2201/165; A61H 2201/5061; A61H 2201/5071;
(Continued)

(56) References Cited

U.S. PATENT DOCUMENTS 3,780,817 A    12/1973  Videon
6,276,214 B1    8/2001  Kimura et al.
(Continued)

FOREIGN PATENT DOCUMENTS

EP    2783834 A1    10/2014
EP    2957225 A1    12/2015
(Continued)

OTHER PUBLICATIONS

International Searching Authority, International Search Report and Written Opinion for International Application No. PCT/EP2016/053239, dated Mar. 30, 2016, 12 pages, European Patent Office, Netherlands.
(Continued)

*Primary Examiner* — Thiem D Phan
(74) *Attorney, Agent, or Firm* — Alston & Bird LLP (57) ABSTRACT

The method for producing the strain gauge device (10) comprises a first stop of producing the band (12). The band (12) has flexibility at least in the measuring zone (36). Then a sensor (22) comprising at least one measuring strand (30) and changing electrical resistivity in dependence of the strain is produced and arranged on or in the band (12) without pre-tension. Afterwards the shape of the band (12)
(Continued)

is changed into a retaining working shape and thereby the measuring strand (30) is stretched to an amount of pretension.

34 Claims, 5 Drawing Sheets

(51) Int. Cl.
*A61B 5/00* (2006.01)
*G01L 1/22* (2006.01)

(52) U.S. Cl.
CPC ............ *G01L 1/2287* (2013.01); *G01L 5/101* (2013.01); *A61B 2562/0261* (2013.01); *A61B 2562/0285* (2013.01); *A61B 2562/12* (2013.01); *Y10T 29/49103* (2015.01)

(58) Field of Classification Search
CPC .............. A61H 31/005; A43C 11/1493; A63B 2071/0663; A63B 2220/833; A63B 2225/09; G01L 5/10; G01L 5/108; G01L 1/22; G01L 1/2287; G01D 11/245; Y10T 24/44231; Y10T 29/49826; Y10T 29/49103
USPC ........ 29/621.1, 592.1, 593, 595, 610.1, 621, 29/846
See application file for complete search history.

(56) References Cited

U.S. PATENT DOCUMENTS

| 9,592,007 | B2 * | 3/2017 | Nuovo ................. A61B 5/0022 |
| 9,848,781 | B2 | 12/2017 | Suesstrunk et al. |
| 9,993,050 | B2 * | 6/2018 | Lee ...................... A44C 5/2076 |
| 2010/0210956 | A1 | 8/2010 | Im |
| 2011/0166461 | A1 | 7/2011 | Süsstrunk et al. |
| 2013/0144176 | A1 | 6/2013 | Lec |

FOREIGN PATENT DOCUMENTS

| JP | S511987 B1 | 1/1976 |
| JP | S57104908 U | 6/1982 |
| JP | 2012-500033 A | 1/2012 |
| JP | 2012-137354 A | 7/2012 |
| WO | WO 2010/017973 A1 | 2/2010 |
| WO | WO 2014/197760 A1 | 12/2014 |

OTHER PUBLICATIONS

Japanese Patent Office, Japanese Office Action for Patent Application No. 2017-566194, dated Aug. 29, 2019, (17 pages), Japan.

* cited by examiner

METHOD FOR PRODUCING A STRAIN GAUGE DEVICE

CROSS REFERENCE TO RELATED APPLICATIONS

This application is a National Stage Application, filed under 35 U.S.C. 371, of International Application No. PCT/EP2016/053239, filed Feb. 16, 2016, which claims priority to European Application No. 15158800.1, filed Mar. 12, 2015; the contents of both of which as are hereby incorporated by reference in their entirety.

BACKGROUND

Related Field

The present invention is related to a method for producing a strain gauge device and an equipment for continually measuring the blood pressure of a user for monitoring purposes, each according to the claims provided herein.

Description of Related Art

U.S. Pat. No. 6,276,214 discloses strain sensors formed from conductive particle-polymer composites. One method to make the strain sensors is a molding process wherein conductive particles such as carbon are mixed with a molten polymer in a mixer such as a kneader, and the composite is made in the shape of a film. Electrodes can be applied during or after the molding process. Another method is printing wherein a polymer is dissolved in a solvent and then conductive particles are mixed with the solution; and this solution, composed of conductive particles, the polymer and the solvent, is called ink. The sensors are made by printing a base film where electrodes have been printed already. It is also possible to make the sensors by dispensing conductive particles in the mixture of thermocured plastics and their hardening agents and then molding them.

Document US 2011/0166461 A1 discloses an equipment and a method for continually measuring the blood pressure for monitoring purposes. The equipment has at least one pressure sensor disposed for being places onto the surface of the body of the user and being held attached thereto by means of a band. The attachment force is selected such that a pressure signal from the pressure sensor contains variations caused by the pulse. An attachment pressure sensor or a band tension sensor generates an electrical signal depending on the attachment pressure. A microprocessor determines the diastolic and systolic blood pressure values from the pressure signal, taking into account the signal from the attachment pressure sensor or the band tension sensor. Once the equipment has been attached to a suitable location on an extremity of the user, the necessary armband tension is set by loosening or tightening the band.

The strain gauge device disclosed in the older European patent application no. 14 002 103.1 (publication EP 2 957 225 A1) comprises an elastic band, the strain of which is to be measured. The sensor comprises at least one elongated measuring strand changing electrical resistivity in dependence of the strain of the band. The measuring strand is mounted with pre-tension to the unstressed band by means of a layer of glue disposed between the sensor and the band. An equipment for continually measuring the blood pressure of a user comprises at least one such strain gauge device. Fixing the sensor with pre-tension demands effort and skill.

BRIEF SUMMARY

It is an object of the present invention to propose a simplified method for producing a strain gauge device and an equipment for continually measuring the blood pressure of a user for monitoring purposes comprising a strain gauge device produced accordingly.

The method according to the present invention comprises a step of producing a band defining an upper side, an underside and having flexibility in a measuring zone. The measuring zone is preferably built by a section of the band having higher flexibility than the residual sections of the band on both sides of the measuring zone.

Preferably, the measuring zone takes the whole width of the band.

A tensioning direction runs in the longitudinal direction of the band.

The method further comprises a step of producing a sensor comprising at least one elongate measuring strand changing electrical resistivity in dependence of the strain. The sensor is arranged at or in the band such that the measuring strand runs at least almost in the tensioning direction i.e. the longitudinal direction of the band from one end of the measuring zone to the other end of the measuring zone. Preferably, the sensor and thus the measuring strand are fixed to the band at least in regions of the band directly following the measuring zone.

The strain of the band is to be measured by means of the sensor.

In production the sensor is arranged in or on the band without pre-tension. This feature allows a simplified manufacturing and enables the production of the band and the sensor by 3-D printing, preferably in one production stage, or by a layered manufacturing method.

In a further step the shape of the band, in or at which the sensor is fixed, is changed into a retaining working shape, at least in the measuring zone, such that the sensor, i.e. the measuring strand is pre-tensioned to a desired amount of pre-tension. Pre-tensioning ensures that in use the measuring strand is always tensioned.

Retaining working shape means that after the change of the shape of the band into the retaining working shape, at least in the measuring zone, the band does not return to the original shape or form. Thus, the measuring strand remains pre-tensioned.

In use of the strain gauge device the amount of pre-tension defines a lower limit of a working range of the sensor. The pre-tension enables the working of the sensor in an ideal working range.

An upper limit of the working range is given by the elastic limit of the band and the sensor or the characteristics of the sensor.

In use of the strain gauge device the strain of the band is measured while stretching in the tensioning direction.

Preferably the sensor is arranged between a bending line of the band and the upper side of the band or on the upper side of the band. Thus, when bending the band and especially the measuring zone along the longitudinal direction in a direction towards the underside into the working shape the sensor is pre-tensioned as the sensor is arranged radially outwardly of the bending line.

As a matter of completeness it is mentioned that the sensor is preferably supported by the band before, during and after the bending of the band by the band, preferably over at least almost the whole length of the measuring strand.

It is also possible to stretch the band, at least the measuring zone in the longitudinal direction for changing the shape into the retaining working shape and thereby pre-tensioning the sensor. In this case, the band is designed such that at least the measuring zone does not return to the original form.

For that purpose it is possible to use shape memory polymer or polymer networks as known for example from document EP 2 783 834 A1 for the production of the band, especially in the measuring zone.

Preferably, the band is produced at least in the measuring zone so as to be curved along the longitudinal axis in a direction towards the upper side; i.e. a concave curve. Thus, pre-tension is attainable by bending the band, especially the measuring zone, in a plane or in a convex curvature.

Preferably, the band is stiffened or reinforced adjacent to the measuring zone. The sensor is fixed to these stiffened or reinforced regions and the measuring strand runs from one of these stiffened or reinforced regions to the other one. Preferably, the measuring strand is free of fixation to the measuring zone between the two stiffened or reinforced regions. But on the other hand it can be preferred that the sensor is also fixed to the band in the measuring zone between the stiffened or reinforced regions so that the sensor is at least almost area wide attached to the band.

The band is preferably produced as a cell array structure. It is possible that the stiffness of the cell array structure in the measuring zone is the same as in regions outside the measuring zone. However, a lower stiffness in the measuring zone is preferred. This leads in use of the stain gauge device to a bigger elongation in the measuring zone than in the regions outside the measuring zone per unit of length and thus to a more precise measurement of the strain and thus the force with which the band is stressed.

Preferably, the cell size of the cells in the measuring zone is larger than a cell size outside the measuring zone. Larger cells have a lower stiffness than smaller cells. It is possible to produce the cell walls of the larger cells smaller than the cell walls of the smaller cells to reduce the stiffness in the measuring zone. However, it is preferred that the thickness of the walls of all cells is at least almost equal. This leads to a simpler production.

The cells preferably have a similar shape in and outside the measuring zone. But it is also possible to have different shapes.

Preferably, the cell array structure is produced in a honeycomb or an auxetic form at least in the measuring zone.

When using a cell array structure at least in the measuring zone, to prevent the return of the band from the changed shape (for pre-tension) to the original shape it is possible to insert foam material in cells, preferably in all cells of the cell array structure in the measuring zone.

In the changed shape of the band, the foam material lies against the walls of the respective cells.

In case that foam material is not inserted in all cells, it is preferred that foam material is inserted in the cells of at least one row of cells—preferably at least two rows of cells—running at least approximately in the longitudinal direction. In such a row of cells the respective cells follow one another as seen in the longitudinal direction. Preferably, the row of cells is uninterrupted and runs from one end of the measuring zone to the other end.

Preferably closed-cell foam is used.

It is possible to bond the foam material to only one wall of the cells.

Further, it is possible to add at least in the measuring zone, for example also by a 3D-pringing process, stop arms, having a free end, to walls of cells. The stop arm spans the respective cell and the free end cooperates with the other wall of the respective cell and supports this other wall in the changed shape of the band.

In case that stop arms are not assigned to all cells, it is preferred that stop arms are assigned to the cells of at least one row of cells—preferably at least two rows of cells—running at least approximately in the longitudinal direction. In such a row of cells the respective cells follow one another as seen in the longitudinal direction. Preferably, the row of cells is uninterrupted and runs from one end of the measuring zone to the other end.

Preferably, an electronic unit is arranged in or on the band whereby electrical connecting lines connect the sensor and the electronic unit. The electronic unit can serve to feed the sensor with an electrical current and to measure the electrical tension between the two ends of the sensor or vice versa. Thus, the electrical resistivity of the sensor in dependence of the strain can be measured. Further, the electronic unit can be designed for the processing of the signals generated by the sensor and to communicate with an external device for transmitting the measuring result.

For example, the electronic unit can comprise a microprocessor for continually measuring the blood pressure of a user for monitoring purposes, as that is known from document WO 2010/017973 A1, the disclosure of which is introduced into the present disclosure by reference.

The band, the sensor and if applicable the connecting lines are particularly preferably produced by 3-D printing or layered manufacturing methods. Layered manufacturing methods may be employed such as fusion deposition modeling (FDM), where a thermoplastic may be melted and deposited in thin layers in order to build up a 3D structure.

Preferably, the shape of the band in the measuring zone into the retaining working shape is changed such that the amount of pre-tension is between 5% and 70%, preferably between 7% and 20%, most preferably at least approximately 10%.

Preferably, using for the production of the sensor a material that comprises, preferably is a mixture of a thermoplastic elastomer (TPE) and carbon black particles in the amount of 10 wt-%-60 wt-%, preferably of 40 wt-%-55 wt-%, more preferably at least approximately 50 wt-%.

Preferably, for the production of the sensor a material is used that comprises, preferably is a mixture of a thermoplastic elastomer (TPE) and graphene or nanotube particles in the amount of 2 wt-%-10 wt-%, preferably of about 5 wt-%.

Preferably, for the production of the sensor a material is used that comprises, preferably is a mixture of a thermoplastic elastomer (TPE) and electrical conductive particles, preferably particles of a metal or other inorganic material, preferably copper, silver, indium tin oxide or fluorine tin oxide, in the amount of 10 wt-%-60 wt-%, preferably 40 wt-%-55 wt-%, more preferably at least approximately 50 wt-.

The sensor is preferably produced as to have a thickness equal to or less than 0.7 mm, preferably between 0.1 and 0.5 mm, most preferably of at least approximately 0.3 mm.

Preferably, the measuring strand of the sensor is produced to have a width between 0.1 mm and 2 mm, preferably between 0.4 mm and 1 mm, and a length between 7 mm and 20 mm, preferably 8 mm and 15 mm, especially of at least approximately 10 mm.

The sensor is preferably produced to comprise at least two measuring strands arranged at least approximately parallel over the length of the measuring zone and electrically connected in series, preferably particularly two measuring stands connected at one end by means of a common connecting strand so that the sensor has the shape of an U.

Preferably, the sensor is produced to have a reversible flexibility of at least 100/150, preferably of at least 100/200, in particular of at least 100/250.

The band is preferably produced to have flexibility following the sensor on both sides, as seen in the tensioning direction, for at least approximately 10 mm, preferably for at least 15 mm to 20 mm. However, that flexibility is preferably smaller than the flexibility of the measuring zone.

The present invention further concerns an equipment for continually measuring the blood pressure of a user for monitoring purposes. The equipment has at least one pressure sensor suitable for resting against a site on the external surface of the body of the user, continuously measuring the pressure at the site influenced by the blood pressure and generating a corresponding electrical pressure signal. The equipment comprises a strain gauge device produced according to the present invention. The band is suitable for encompassing the body and holding the pressure sensor against the surface at the site with safe, functional contact and the strain gauge device is suitable for continuously measuring the strain of the band and generating a corresponding electrical band-tension signal. The equipment comprises an electronic circuit with a current supply, a microprocessor for establishing a diastolic and a systolic blood-pressure value from the contact-pressure signal taking into account the band-tension signal, and an output device for displaying or outputting the blood-pressure values.

The equipment is preferably designed as disclosed in document WO 2010/017973 A1, the disclosure of which is herewith introduced by reference, whereby the strain gauge device corresponds to the present invention.

Preferably, the electronic circuit energizes the strain gauge device, i.e. the sensor with a predetermined current and measures the voltage as described above.

BRIEF DESCRIPTION OF THE FIGURES

The invention will be explained in more details on the basis of the embodiments illustrated in the drawing, in which in a purely schematic fashion.

DETAILED DESCRIPTION OF VARIOUS EMBODIMENTS

Figure 1:
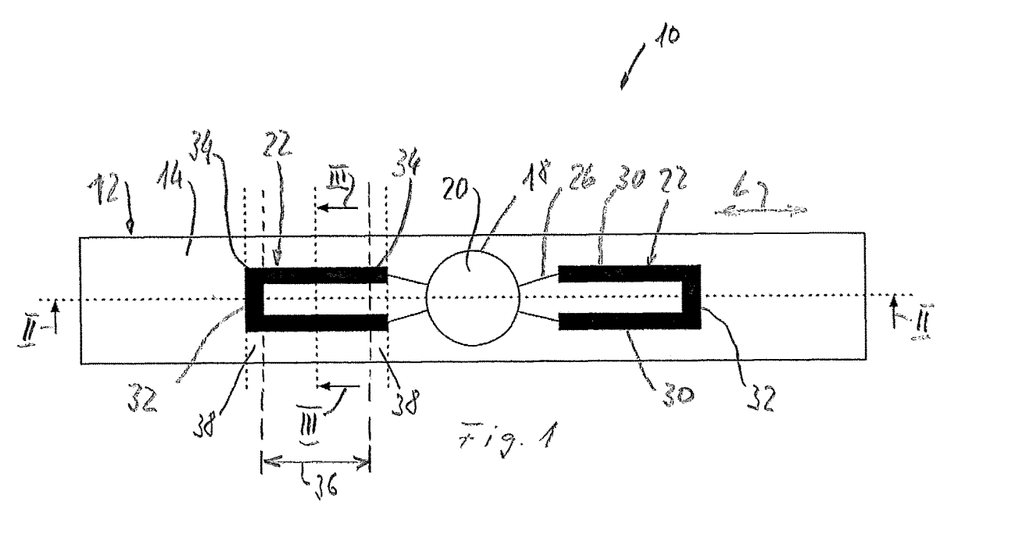
FIG. 1 shows a first embodiment of a strain gauge device in topview having a band, two sensors and an electronic unit.
Figure 2:
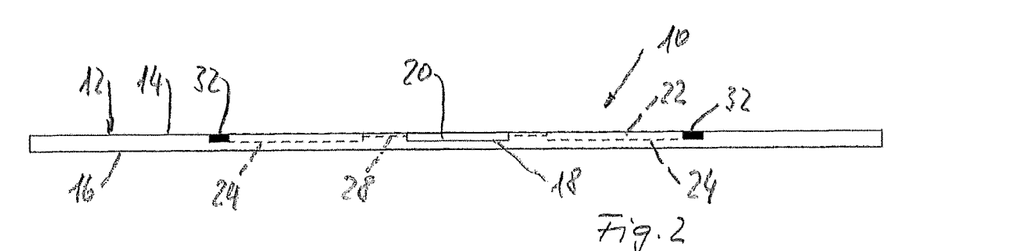
FIG. 2 shows a longitudinal section of the first embodiment along cutting line II-II of FIG. 1.
Figure 3:
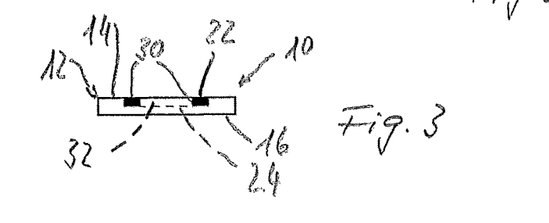
FIG. 3 shows a cross section of the first embodiment along cutting line III-III of FIG. 1.

FIGS. 1 to 3 show a strain gauge device 10 produced according to the present invention. The strain gauge device 10 comprises a flat band 12 having an upper side 14 and an underside 16 and defining a longitudinal direction L.

The band 12 exhibits on its upper side 14, and approximately in the middle as seen in the longitudinal direction L and in cross direction, a circular recess 18 in which an electronic unit 20 is arranged.

As seen in the longitudinal direction L, on each side of the electronic unit 20 a U-shaped sensor 22 is arranged in a correspondingly formed sensor recess 24 on the upper side 14 of the band 12. The two sensors 22 are mirror-inverted arranged in a distance to the electronic unit 20.

From the two free ends of each sensor 22 an electrical connection line 26 or path runs to the electronic unit 20. The connections lines 26 are disposed in respective channels 28 connecting the sensor recesses 24 with the recess 18 for the sensors 22.

Each of the sensors 22 has two measuring strands 30 running parallel to each other in the longitudinal direction L. The two measuring strands 30 of each sensor 22 are connected in series by means of a common connecting strand 32.

The whole sensor 22 is made integrally in one piece whereby the ends of the measuring strands 30 averted from the electronic unit 20 are connected to each other by the connecting strand 32 and the end of the measuring strands facing the electronic unit 20 are connected to the electronic unit 20 by means of the connection lines 26.

The two end regions 34 of each measuring strand 30 and the connecting strand 32 are fixed to the band 12, preferably by means of a material bond by using affine materials for the band 12 and the sensors 22.

It is also possible to fix the sensors 22 thus the measuring strands 30 area wide to the band 12.

The band 12 constitutes measuring zones 36 running, as seen in the longitudinal direction L, from the one end region 34 of the measuring strands 32 to the other end region 34 whereby each sensor 22 runs in the longitudinal direction L over the dedicated measuring zone 36. The two measuring zones 36 take the whole width of the band 12.

At the end regions 34 of the measuring strands 32 the band 12 can be reinforced or stiffened, preferably in the form of a reinforced region 38 running in the form of a band across the band 12. The reinforcement can be produced by a film of a material having a lower elasticity than the material of the band 12 whereby preferably these two materials are affine so as to build a material bond.

In the measuring zone 36 the band 12 has flexibility. Outside the measuring zone 36 the band can also have flexibility whereby in a preferred manner the flexibility outside the measuring zone 36 is lower than in the measuring zone 36.

In a preferred embodiment, the band 10 has flexibility following the sensors 22 on both sides, as seen in the longitudinal direction L, for at least 10 mm. However, that flexibility is preferably lower than the flexibility of the measuring zone 36.

A tensioning direction of the band 12 runs in the longitudinal direction L. The strain of the band 12 is to be measured by means of the sensors 22 in use of the strain gauge device 10.

The stiffness and flexibility of the structured material of the band 12 can be tuned in different ways in relationship to the material of the sensors 22.

Preferably, the flexibility of the sensor 22 and thus the measuring strands 32 is always higher than the flexibility of the band 12; i.e. the modulus of elasticity of the sensor 22 is preferably smaller than that of the band 12.

The strain gauge device 10, especially the band 12 and the sensors 22 can be produced by a known layered manufacturing method. Thereby, the stiffness of the band 12 can be tuned by increasing the thickness of a deposited layer in the zones of higher stiffness and by reducing the thickness of a deposited layer in the zones of smaller stiffness, i.e. at least in the measuring zones 36.

It is also possible to use affine materials but having different stiffness in the receptive zone.

The strain gauge device 10 can also be produced by using a known 3D-printing method. Thereby, preferably a 3D-printing device having at least two nozzles, one for the structural material of the band 10 and the other one for the structural material of the sensors 22 is used.

Preferably, a 3D-printing device having three nozzles is used, the third nozzle for the material of the electrical connection lines 26. This could be a conductive ink, for example based on silver-nanotubes or particles, or a conductive polymer based on graphene, carbon nanotubes, etc.

For the production of the band 12 and the sensors 22 the materials as disclosed in the introductory portion and in the claims can be used. Preferably, thermoplastic elastomer (TPE) is used.

The band 12 is preferably 10 mm to 20 mm in width.

Preferably, the sensor 22 has a thickness of about 0.5 mm and a length of about 10 mm to 15 mm and the measuring strands 30 and the connecting strand 32 have a width of about 5 mm In any case, the sensors 22 are produced and attached to the band 12 without pre-tension in either direction, especially in the longitudinal direction L.

But after the production of the band 12 and the sensors 22 the shape of the band 12 is changed in such a retaining working shape that the measuring strands 30 of the sensors 22 are stretched to an amount of pre-tension.

Preferably, the pre-tension is between 10% and 20% as measured in the longitudinal direction L; this applies to all embodiments.

For that purpose, it is possible to use for the band 12 a shape memory polymer or polymer network and to extend the band 12 at least in the measuring zones 36 in the longitudinal direction L into the retaining working shape as for example disclosed in document EP 2 783 834 A1, the disclosure of which is herewith introduced by reference.

Another option is to stretch the band 12 under tensile loading to expand the structure so that a permanent deformation can then exist in the material of the band, in particular if a cell geometry is designed in such a way.

Figure 4:
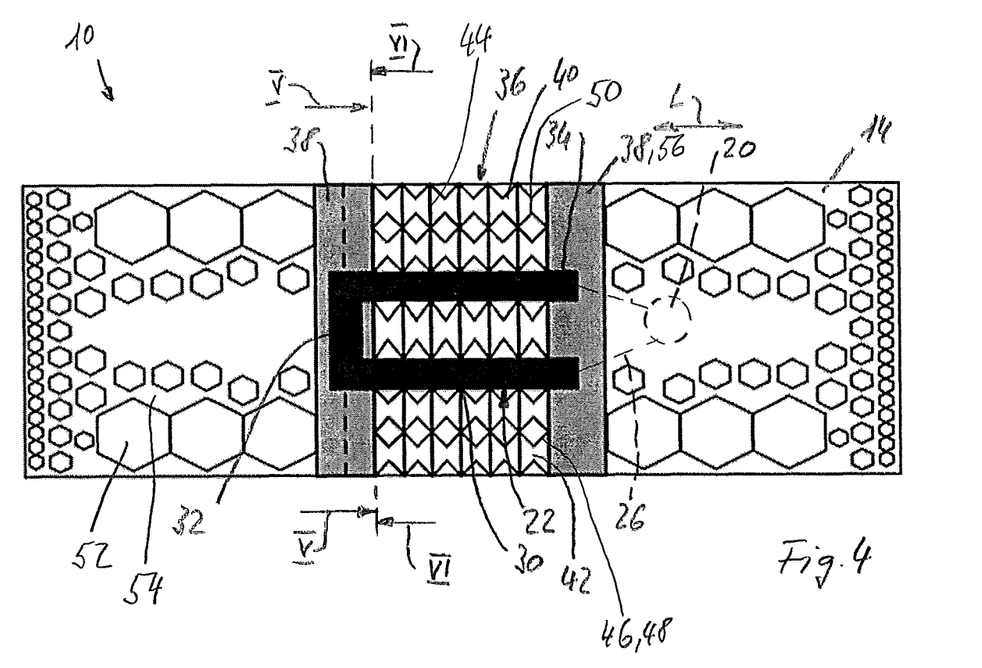
FIG. 4 shows in top view a second embodiment of the strain gauge device having one sensor, wherein the band is produced as a cell array structure.
Figure 5:
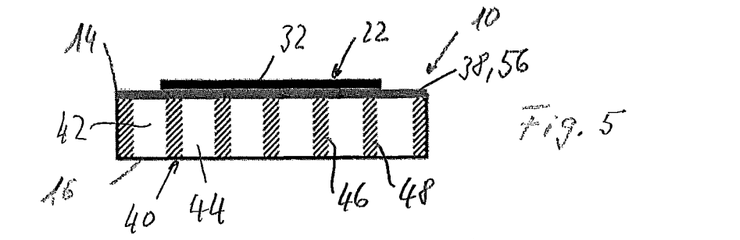
FIG. 5 shows a cross section of the second embodiment along cutting line V-V of FIG. 4.
Figure 6:
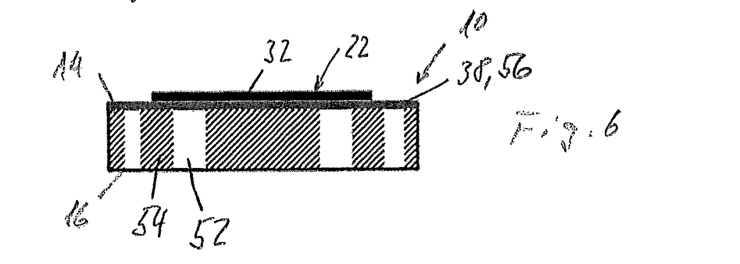
FIG. 6 shows a cross section of the second embodiment along cutting line VI-VI of FIG. 4.

In the embodiment of the strain gauge device 10 shown in FIGS. 4 to 6 the band 12 is produced in the form of a cell array structure 40. For the production of such a band 12 preferably a 3D-printing method is used.

The cells 42 of the cell array structure 40 are open at the upper side 14 and the underside 16 of the band 12. Thus, the cells 42 run through the band 12 from the upper side 14 to the underside 16.

In the measuring zone 36 the cells 42 have the same shape and cell walls 44 running at right angles to the longitudinal direction L. These cell walls 44 are in each case common to two cells following one another in the longitudinal direction L, whereby the cell walls 44 of the cells 42 arranged in a row running at right angles to the longitudinal direction are connected to one another and are located in a common plane.

The walls 44 of each cell 42 are connected to one another by means of two accordion partitions 46 having two flat wall parts 48 being connected to one another and the respective walls 44 by means of integral hinges 50.

The accordion partitions 46 of each cell 42 are directed towards each other such that the wall parts 48 enclose an angle of about 90°.

The cell array structure 40 on both sides of the measuring zone 36, as seen in the longitudinal direction L, is different to that in the measuring zone 36. The flexibility in the measuring zone 36 is higher than in the residual zones of the band 12 outside the measuring zone 36.

Outside of the measuring zone 36 the band 12 comprises a multiplicity of hexagonal breakthroughs 52. By varying the cross section of the breakthroughs 52 and the thickness of the wall 54 between breakthroughs 52 the flexibility of the band 12 can be set.

Small cross sections of the breakthroughs 52 result in a higher stiffness than bigger cross sections. Thick walls 54 increase the stiffness relative to thin walls 54.

In the embodiment shown in FIGS. 4 to 6 the band 12 has, subsequent the measuring zone 36 on both sides, alongside each of the margins a row of three breakthroughs 52 having big crosssection. A middle part has no breakthroughs and there is between the middle part and the breakthrough 52 along the margins in each case a further row of breakthrough 56 but with a smaller crosssection. Thus, in the middle part the band has a small flexibility compared with the flexibility of the measuring zone 36. But, in the margin regions the flexibility is given for high wearing comfort of the strain gauge device 10 when worn by a user.

Subsequent the measuring zone 36 the band 12 has on the upper side 14 a stiffening or reinforcing covering 56 running in the form an band as a film or tape over the whole width of the band 12. This covering builds reinforced or stiffened regions 38 to which the end regions 30 of the measuring strands 30 of the sensor 22 are fixed. The sensor 22 has the same structure as the sensors 22 shown in and described in connection with FIGS. 1 to 3.

In the embodiment shown in FIGS. 4 to 6 the measuring strands 30 are preferably not fixed to the cell array structure 40 in the measuring zone 36.

The sensor 22 is produced and fixed to the band 12 without pre-tension. After the production of the band 12 and the thereto fixed sensor 22 the band is stretched in the longitudinal direction so that the wall parts 48 of the accordion partition 46 are aligned at least approximately in the longitudinal direction.

This change of the shape of the band 12 in the measuring zone 36 stretches the measuring strands 30 to the desired amount of pre-tension.

To prevent the move back of the band 12 from the changed shape in the original shape it is possible to insert foam material in cells 42, preferably in all cells 42 of the cell array structure 40 in the measuring zone. In the changed shape of the band 12, the foam material lies against the walls 44 of the respective cells 42. Preferably closed-cell foam is used. It is possible to bond the foam material to only one wall 44 of the cells 42. Further, it is possible to add, for example also by a 3D-pringing process, stop arms, having a free end, to walls 44. The stop arm spans the respective cell 44 and the free end cooperates with the other wall 44 of the respective cell 42 and supports this other wall 44 in the changed shape of the band 12. These possibilities can be used with all cell array structures 40.

In the embodiment shown in FIGS. 4 to 6 the electronic unit 20 can be disposed in the middle region of the band 12 at the right side outside the measuring zone 36.

Figure 7:
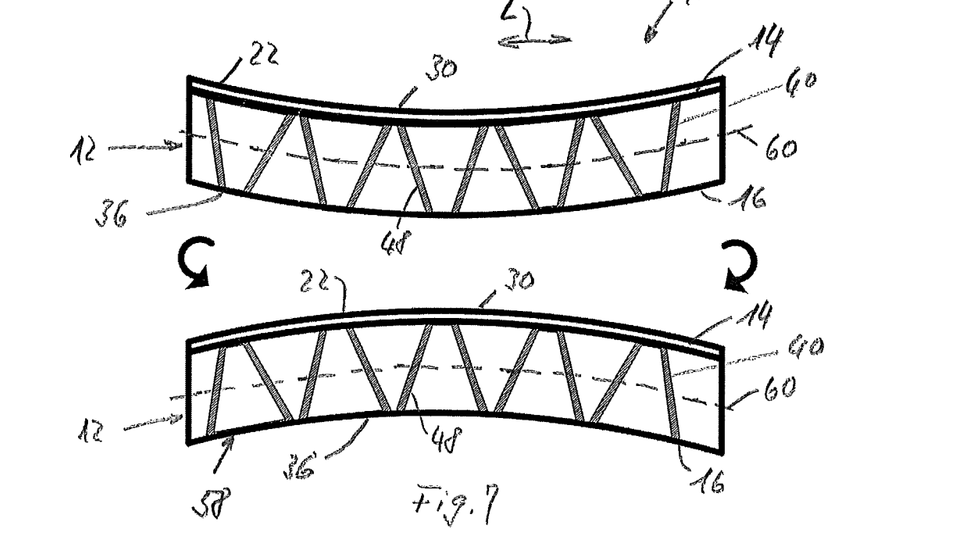
FIG. 7 shows a longitudinal section of a measuring zone of the band and the sensor of the strain gauge device, in the upper part after production of the band and the sensor and in the lower part after changing the shape of the band for pre-tensioning the sensor.

FIG. 7 shows a further possibility for changing the shape of the band 12 in the measuring zone 36 into the retaining working shape 58.

The upper part of FIG. 7 shows the measuring zone 36 of the band 12 during production before the change of the shape.

The band 12, at least in the measuring zone 36, is produced—for example by a 3D-printing method—so as to be curved along the longitudinal axis, i.e. longitudinal direction L, in a direction towards the upper side 14. Thus the measuring zone 36 is concave.

The sensor 22 is arranged on the upper side 14 of the band 12 and produced and fixed without pre-tension.

A bending line 60 of the band is denoted by a broken line.

Walls 48 of the cell array structure 40 in the measuring zone 36 are shown in profile.

For changing the shape of the band 12, the band 12 is bent into a convex curvature as indicated by the arrows and shown in the lower part of FIG. 7. The retaining working shape in which the measuring strands 30 are and thus the sensor 22 is pre-tensioned to the desired amount is denoted by reference numeral 58.

A such production of the band 12 and sensor 22 and a such bending procedure can also be used for the embodiment of FIGS. 1 to 6.

In the embodiment shown in FIG. 7 it is possible to prevent the move back of the band 12 from the changed shape in the original shape by means of foam material or stop arms as described above, too.

Figure 8:
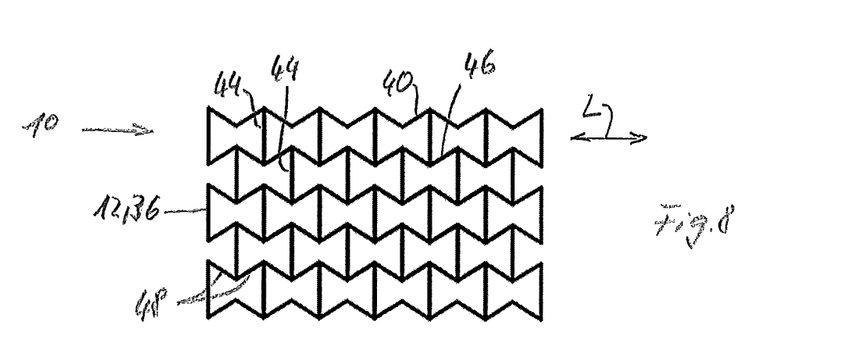
FIG. 8 shows a top view of the measuring zone of the band with a cell array structure in an auxetic form after production of the band and before changing the shape of the band for pre-tensioning the sensor.
Figure 9:
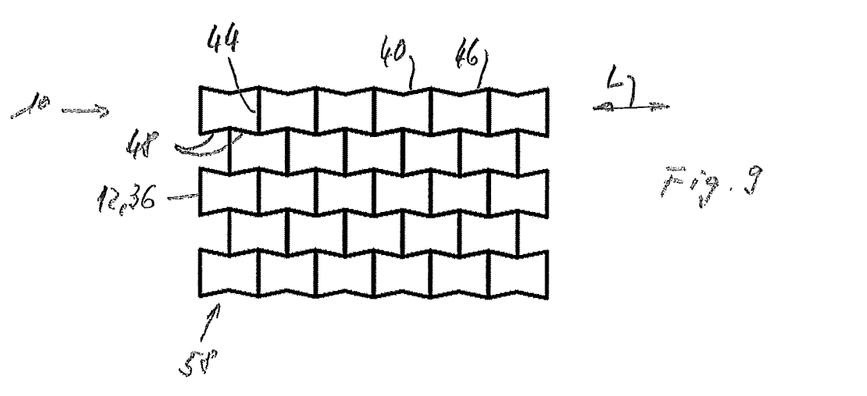
FIG. 9 shows a top view of the cell array structure of FIG. 8 after changing the shape of the band for pre-tensioning the sensor.

FIGS. 8 and 9 show the cell array structure 40 in the measuring zone 36 in an auxetic form, in FIG. 8 before and in FIG. 9 after changing the shape of the band 12 into the retaining working shape 58.

Accordion partitions 46 run in the longitudinal direction L whereby adjacent accordion partitions 46 are laterally reversed designed.

Cell walls 44 are in each case connected to the integral hinges 50 connecting two wall parts 48 and in fact there where adjoining wall parts 48 enclose an acute angle.

When stretching the measuring zone 36 in the longitudinal direction L the accordion partitions 46 move in essentially straight planes running in the longitudinal direction L as shown in FIG. 9.

Also in the embodiment shown in FIGS. 8 and 9 it is possible to prevent the move back of the band 12 from the changed shape (for pre-tension) in the original shape by means of foam material or stop arms as described above.

For a such cell array structure 40 the production and shape changing of the strain gauge device 10 as shown in and described in connection with FIG. 7 can also be used.

Figure 10:
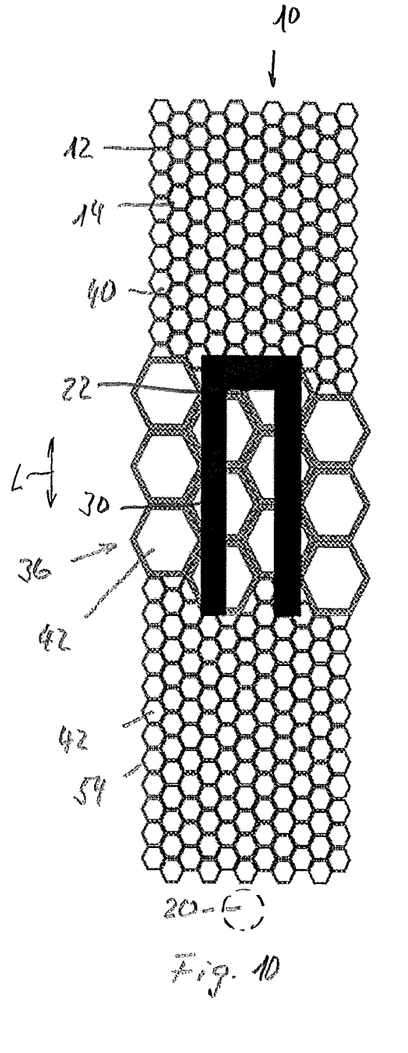
FIG. 10 shows a top view of a third embodiment of the strain gauge device, the band being produced as a cell array structure in honeycomb form.

FIG. 10 shows an embodiment of the strain gauge device 10 with a band 12 produced as a cell array structure in a honeycomb form. The cell size of the cells 42 in the measuring zone 36 is larger, for example about five times larger, than the cell size of the cells 42 outside the measuring zone 36. Thus the flexibility of the band 12 in the measuring zone is greater than in the zones outside the measuring zone 36.

The end regions 34 of the measuring strands 30 and the connecting strand 32 are fixed to the face side of the walls 54 of honeycomb cells of smaller dimensions adjacent the measuring zone 36. They can further be fixed to the face side of the wall parts of the cells 42 of the measuring zone 36 joining the cells of smaller size.

However, it is further possible to reinforce or stiffen the band 12 at least on the upper side 14 in the regions adjoining the measuring zone 36 and to fix the end regions 34 of the measuring strands 32 to these reinforced regions 38.

The electrical connection lines 26 connecting the sensor with the electronic unit 20 can be designed and produced as described below in connection with FIG. 11.

Figure 11:
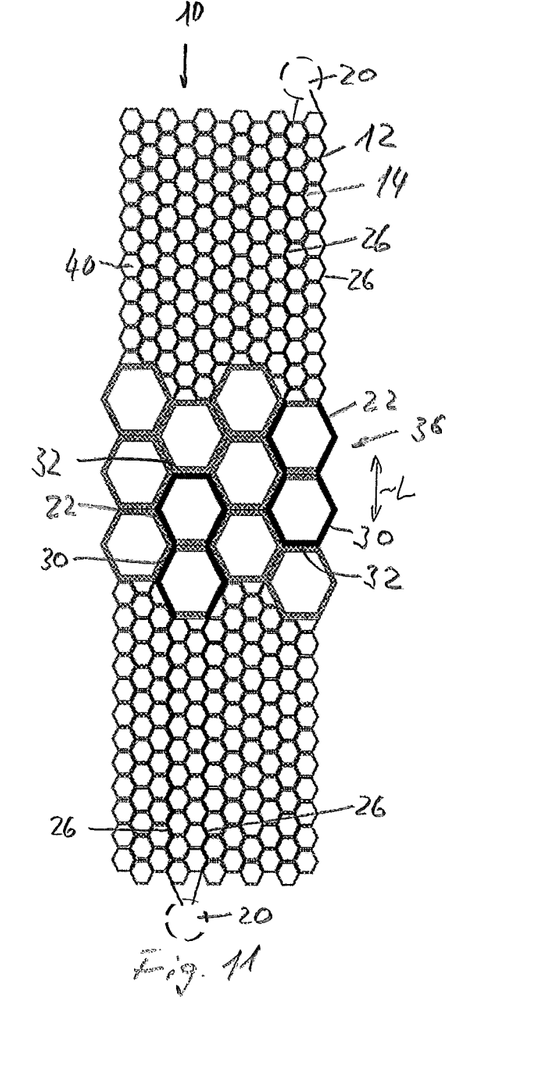
FIG. 11 shows a top view of a forth embodiment of the strain gauge device, the band being produced as a cell array structure in honeycomb form and the sensors being produced as a filament on the upper face side of cells.

The band 12 of the strain gauge device 10 shown in FIG. 11 has the same design as that in FIG. 10.

The two sensors 20 of the strain gauge device 10 shown in FIG. 11 are not anymore designed in a laminar form as shown for example in FIG. 10, but they are designed in the form of a filament fixed to the upper face side of the walls 54 running approximately in the longitudinal direction L of in each case two honeycomb cells 42 following each other in the longitudinal direction in the measuring zone 36. These portions of the filament form the measuring strands 30 of the sensors 22. A connecting strand 32 connecting the measuring strands 30 is arranged at the face side of a wall 54 of the second honeycomb cell running at right angles with respect to the longitudinal direction L.

The electrical connection lines 26 leading from the measuring strands 30 of the sensors 22 to the respective electronic unit 20 are arranged at the upper face side of cell walls 54 of cells 42 outside the measuring zone 36.

The sensors 22 and connection lines 26 of this type can be produced by a 3D-printing method, too.

For changing the shape of the band 12, at least in the measuring zone 36, into the retaining working shape 58 stretching or bending can be used as disclosed above.

The walls 54 of all honeycomb cells 42 can have the same thickness. But it is also possible, as shown in FIGS. 10 and 11, to produce the walls 54 of the cells 42 in the measuring zone 36 thicker than outside. However, the elasticity of the measuring zone 36 remains greater than outside due to the larger cell size.

It is to be noted that the band 12 can be longer than shown in Figures.

It is also possible that the ends of the band 20 are connected with a band extension and/or a lock, preferably this band extension is flexible.

Strain gauge devices 10 according to the present invention are suited for continually measuring physiological parameters of a user such as pulse, breathing, activity of muscles and so on, for monitoring purposes. Thus, they can be vital data monitoring devices.

Figure 12:
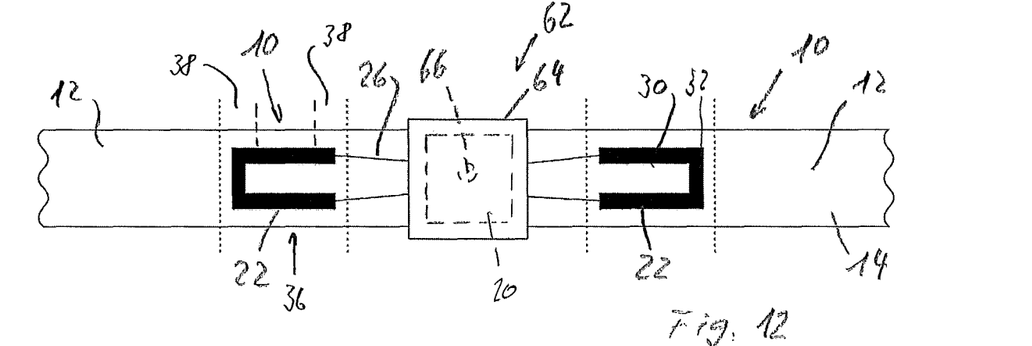
FIG. 12 shows in top view an equipment for continually measuring the blood pressure of a user having two strain gauge devices.

FIG. 12 shows an equipment 62 for continually measuring the blood pressure of a user for monitoring purposes.

The equipment 62 comprises a housing 64 with a bearing plate at the underside beyond which a pressure sensor 66 protrudes. The pressure sensor 66 is suitable for resting against a site on the external surface of the body of the user, in the present case on the surface of an arm, for continuously measuring the pressure at the site influenced by the blood pressure and for generating a corresponding electrical pressure signal.

At the housing 64 the ends of two parts of the band 12 are fixed. The band 18 in form of a wristband is suitable for encompassing the arm and holding the pressure sensor 66 against the surface at the site with safe, functional contact. Each of these two parts of the band 12 constitutes a strain gauge device 10—a so called band-tension sensor—for continuously measuring the tensile stress in the band 12 and generating a corresponding electrical band-tension signal or band-strain signal.

The electronic unit 20 with a current supply, a microprocessor for determination of a diastolic and systolic blood-pressure value from the pressure signal, taking into account the band tension signal/band strain signal, and an output device for displaying or outputting the blood-pressure values, is arranged in the housing 64.

Such an equipment 62—with the exception of different strain gauge devices 10—is disclosed in the document WO 2010/017973 A1 the disclosure of which is hereby introduced into the present disclosure by reference.

In the embodiment shown in FIG. 12 each of the two strain gauge devices 10 comprises band 12 and a sensor 22 attached to the band 12 for measuring the strain and thus the mechanical tension in the band 12. These strain gauge devices 10 are produced according to the present invention. They can be designed according to FIGS. 1 to 11 and the respective disclosure whereby each strain gauge device 10 comprises one sensor 22. The sensors 22 are connected to the electronic unit 20 by means of wires or the electrical connection lines 26.

The sensors 22 change the electrical resistivity in dependence of the applied strain.

For measuring the electrical resistivity of the sensors 22 and thus the change of the electrical resistivity of the sensors 22 in dependence of the stain, the sensors 22 are connected with a current supply or a current source of the electronic unit 20 via the wires or electrical conductor lines 26 so that the sensors 22 are flown through by a predefined electrical current. A voltage measuring portion of the electronic unit 20 continually measures the voltage between the wires or electrical connection lines 26, respectively, and inputs the voltage-values to the microprocessor. In this case, the voltage between the two ends of the sensors 22, i.e. the wires or electrical connection lines 26 is proportional to the electrical resistivity. Thus, a simple measurement of this voltage delivers a proportion of the strain.

In the equipment 62 as shown in FIG. 12, the electrical band-tension signals/band-strain signals produced by the sensors 22 of the two strain gauge devices 10 are preferably independently analysed and compared by the microprocessor in order to enhance the reliability and thus then accuracy of the blood pressure values.

However, the equipment 62 can be equipped with only one strain gauge device 10.

Figure 13:
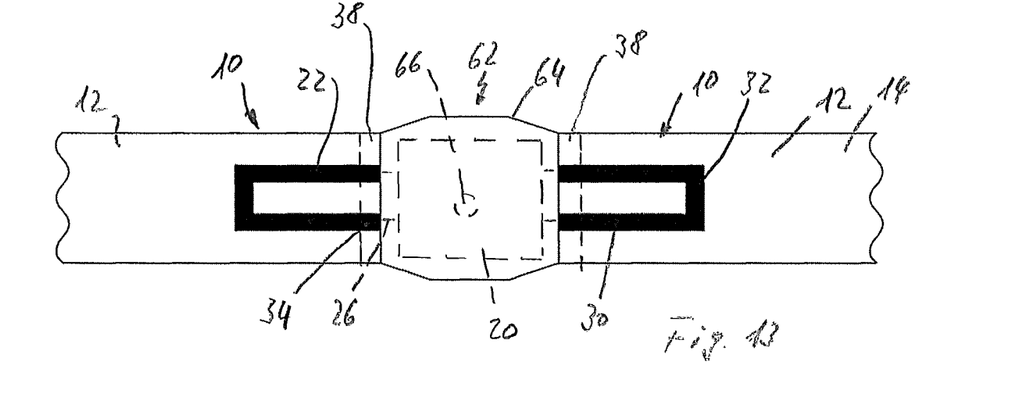
FIG. 13 shows in top view a further embodiment of the equipment for continually measuring the blood pressure of a user having two strain gauge devices.

The equipment shown in FIG. 13 corresponds to that of FIG. 12 with the difference that the free end regions 34 of measuring strands 32 of the sensors 22 are situated just adjacent the housing 64. The strain gauge devices 10 can be designed such as shown in FIG. 4, 10 or 11 whereat the band 12 ends and is connected with the housing 64 with the stiffened regions 38 to which the free end regions 34 of the measuring strands 30 are fixed.

Wires or electric connection lines 26 connect also in this embodiment the electronic unit 20 with the sensors 22.

Figure 14:
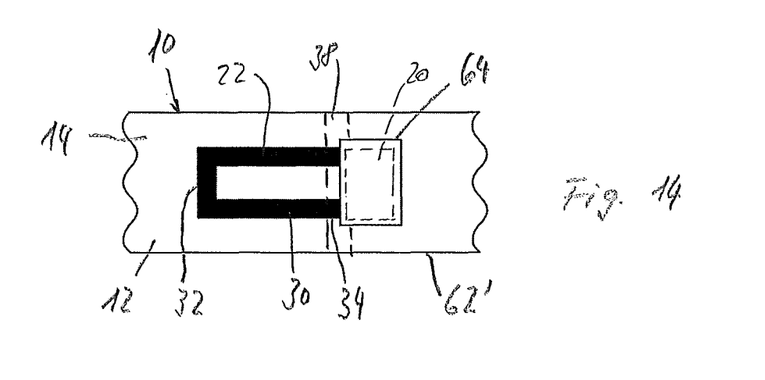
FIG. 14 shows in top view a vital function data device having one strain gauge device.

The equipment 62' shown in FIG. 14—also a vital function data device as the equipment 62—comprises a strain gauge device 10 produced according to the present invention. It can comprise one sensor 22 as also shown in FIGS. 4 and 10 or one of the sensors 22 shown in FIG. 11.

The sensor 22 can be arranged at a distance to the electronic unit 20 or directly next to the electronic unit 20 as disclosed in connection with FIG. 13.

The electronic unit 20 is preferably arranged in a housing 64' that is arranged in the band 12 as for example shown in FIG. 1 or on the upper side 14 of the band 12.

The band 12 is suitable for encompassing the external surface of the body of the user at a desired site and with tensile stress so that the vital function data device, i.e. the equipment 62' is safely held at the site influenced by the respective function of the body of the user to be monitored.

The strain gauge device 20 is in this case as so called band-tension sensor for continuously measuring tensile stress in the band 12 and generating a corresponding electrical band-tension signal or band-strain signal.

The electronic unit 20 with the current supply, the microprocessor for determination of desired values from the band-tension/band-strain signal and the output device for displaying or outputting the values, is arranged in the housing 64.

For measuring the electrical resistivity of the sensor 22 and thus the change of the electrical resistivity of the sensor 22 in dependence of the strain, the sensor 22 is connected with the current supply so that a defined electrical current flows through the sensor 22. The electronic unit 20 comprises means for measuring the voltage between the two wires and electrical connection lines 28, respectively, and thus the voltage across the sensors 22.

This voltage is led to the microprocessor and is proportional to the electrical resistivity of the sensor 22 and thus the change of the voltage is also a proportion to the change of the electrical resistivity due to the change of the strain. Thus, a simple measurement of this voltage delivers a proportion of the strain.

Preferably, the two ends of the band 12 as shown in the FIGS. 1 to 14 are connected with an elastic band—i.e. a prolongation—, that is suitable to encompass together with the band 12 the external surface of the body of user.

The amount of pre-tension of the sensors 22 due to the change of the shape of the band 12 defines a lower limit of the working range of the sensors 22. An upper limit of the working range is given by the respective properties of the band.

In use the strain gauge device 10 works in the working range.

The invention claimed is:

1. A method for producing a strain gauge device (10), said method comprising the steps of:
   producing a band (12) having an upper side (14), an underside (16), defining a tensioning direction (L) running in the longitudinal direction of the band (12) and having flexibility in a measuring zone (36),
   producing a sensor (22) comprising at least one elongate measuring strand (30) changing electrical resistivity in dependence of the strain and arranging the sensor (22) without pre-tension at or in the band such that the measuring strand (30) runs at least almost in the tensioning direction from one end to the other end of the measuring zone (36), changing the shape of the band (12) at least in the measuring zone (36) into a retaining working shape (58); and stretching the measuring strand (30) to an amount of pre-tension, whereat the amount of pre-tension defines a lower limit of a working range of the sensor (22).

2. The method according to claim 1, further comprising the step of arranging the sensor (22) at a distance to a bending line (60) of the band (12) towards the upper side (14) and thereafter, for changing the shape of the band (12) in the retaining working shape (58), bending the band (12) at least in the measuring zone (36) along the longitudinal direction (L) in a direction towards the underside (16) so that thereafter the sensor (22) is arranged radially outwardly of the bending line (60).

3. The method according to claim 1, further comprising the step of mounting the sensor (22) to the upper side (14) of the band (12), then, for changing the shape of the band (12) in the retaining working shape (58), bending the band (12) at least in the measuring zone (36) along the longitudinal direction (L) in a direction towards the underside (16) so that thereafter the sensor (22) is arranged radially outwardly of the bending line (60).

4. The method according to claim 2, further comprising producing the band (12) at least in the measuring zone (36) with a curve along the longitudinal direction (L) directed towards the upper side (14).

5. The method according to claim 1, further comprising stretching the band (12) in the longitudinal direction (L) at least in the measuring zone (36) for changing the shape of the band in the retaining working shape (58).

6. The method according to claim 1, further comprising forming stiffened or reinforced regions (38) in the band (12) or on the upper side (14) of the band (12) adjacent the measuring zone (36) and attaching the sensor (22) exclusively to these reinforced regions (38).

7. The method according to claim 1, further comprising attaching the sensor (20) area-wide to the band (12).

8. The method according to claim 1, further comprising producing the band (12) as a cell array structure (40), in the measuring zone (36) the cells (42) having at most the same stiffness than outside the measuring zone (36).

9. The method according to claim 8, further comprising producing the cells (42) in the measuring zone (36) with a larger cell size than a cell size outside the measuring zone (36).

10. The method according to claim 8, further comprising producing the cells (42) having a similar shape in and outside the measuring zone (36).

11. The method according to claim 8, further comprising producing the cells (42) having in the measuring zone (36) a different shape than outside the measuring zone (36).

12. The method according to claim 8, further comprising producing the cell array structure (40) in a honeycomb or an auxetic form.

13. The method according to claim 8, further comprising producing the cells (42) in the measuring zone (36) with a larger cell size than a cell size outside the measuring zone 936), the thickness of the walls of the cells being at least almost equal.

14. The method according to claim 1, further comprising arranging an electronic unit (20) in or on the band (12) and connecting the sensor (22) and the electronic unit (20) by means of electrical connecting lines (26).

15. The method according to claim 1, further comprising producing the band (12) and the sensor (22) via a 3-D printing or layered manufacturing method.

16. The method according to claim 1, wherein the measuring strand (30) is stretched to an amount of pre-tension between 7% and 00%.

17. The method according to claim 1, wherein for the production of the sensor (22) a material is used that comprises a thermoplastic elastomer (TPE) and carbon black particles in the amount of 40 wt-%-55 wt-%.

18. The method according to claim 1, wherein for the production of the sensor (22) a material is used that comprises a thermoplastic elastomer (TPE) and graphene or nanotubes particles in the amount of 2 wt-%-10 wt-%.

19. The method according to claim 1, wherein for the production of the sensor (12) a material is used that comprises a thermoplastic elastomer (TPE) and electrical conductive particles in the amount of 40 wt-% to 55 wt-%.

20. The method according to claim 19, wherein for the production of the sensor (12) a material is used that is a mixture of a thermoplastic elastomer (TPE) and electrical conductive particles.

21. The method according to claim 19, wherein the electrical conductive particles are particles of a metal or other inorganic material.

22. The method according to claim 19, wherein the electrical conductive particles are either copper, silver, indium tin oxide, or fluorine tin oxide.

23. The method according to claim 1, wherein the sensor (22) is produced with a thickness equal to or less than 0.7 mm.

24. The method according to claim 23, wherein the sensor (22) has a thickness of at least approximately 0.3 mm.

25. The method according to claim 1, wherein the measuring strand (30) of the sensor is produced with a width between 0.1 mm and 2 mm and a length between 7 mm and 20 mm.

26. The method according to claim 1, wherein the sensor (22) is produced as to have at least two measuring strands (30) arranged at least approximately parallel over the length of the measuring zone (36) and electrically connected in series.

27. The method according to claim 1, wherein the sensor (22) is produced as to have a reversible flexibility of at least 100/150.

28. The method according to claim 1, wherein the band (12) is produced as to have flexibility following the sensor (22) on both sides, as seen in the tensioning direction and the longitudinal direction (L), for at least approximately 10 mm.

29. The method according to claim 1, wherein for the production of the sensor (22) a material is used that is a mixture of a thermoplastic elastomer (TPE) and carbon black particles in the amount of 40 wt-%-55 wt-%.

30. The method according to claim 1, wherein for the production of the sensor (22) a material is used that is a mixture of a thermoplastic elastomer (TPE) and graphene or nanotubes particles in the amount of 2 wt-%-10 wt-%.

31. The method according to claim 1, wherein the measuring strand (30) of the sensor is produced with a width between 0.4 mm and 1.0 mm, and a length between 8 mm and 15 mm.

32. The method according to claim 1, wherein the sensor (22) is produced as to have two measuring stands (30) connected at one end by means of a common connecting strand (32) so that the sensor (22) has the shape of an U.

33. The method according to claim 1, wherein the sensor (22) is produced as to have a reversible flexibility of at least 100/250.

34. The method according to claim 1, further comprising producing the band (12) as a cell array structure (40), in the measuring zone (36) the cells (42) having a lower stiffness than outside the measuring zone (36).

* * * * *